(12) United States Patent
Trumbull

(10) Patent No.: US 6,454,411 B1
(45) Date of Patent: Sep. 24, 2002

(54) METHOD AND APPARATUS FOR DIRECT PROJECTION OF AN IMAGE ONTO A HUMAN RETINA

(75) Inventor: Douglas Trumbull, Southfield, MA (US)

(73) Assignee: Entertainment Design Workshop LLC, Sheffield, MA (US)

( * ) Notice: Subject to any disclaimer, the term of this patent is extended or adjusted under 35 U.S.C. 154(b) by 0 days.

(21) Appl. No.: 09/441,758

(22) Filed: Nov. 17, 1999

Related U.S. Application Data
(60) Provisional application No. 60/108,722, filed on Nov. 17, 1998.

(51) Int. Cl.$^7$ .................................................. A61B 3/10
(52) U.S. Cl. ..................................................... 351/211
(58) Field of Search ................................ 351/205, 208, 351/209, 210, 211, 214, 237; 345/7, 8, 9; 359/630, 631

(56) References Cited

U.S. PATENT DOCUMENTS

| | | | | |
|---|---|---|---|---|
| 5,467,104 A | * | 11/1995 | Furness, III et al. | 345/8 |
| 5,659,327 A | * | 8/1997 | Furness, III et al. | 345/8 |
| 6,043,799 A | * | 3/2000 | Tidwell | 345/7 |

* cited by examiner

*Primary Examiner*—George Manuel
(74) *Attorney, Agent, or Firm*—McCormick, Paulding & Huber LLP

(57) ABSTRACT

An apparatus for directly projecting an image onto a retina includes an optical source for generating a light beam to be focused on a retina. A projection device sweeps the light beam along the retina in an ellipsoidal pattern such that a higher spatial concentration of light pixels impinge a central portion of the retina than a peripheral portion thereof. A controller is coupled to the optical source and the projection device for modulating the light beam such that a higher temporal concentration of light pixels impinge a central portion of the retina than a peripheral portion thereof.

11 Claims, 8 Drawing Sheets

Convergence
$0°$ = Infinity
$X°$ = Distant Object
$Y°$ = Close Object

METHOD AND APPARATUS FOR DIRECT PROJECTION OF AN IMAGE ONTO A HUMAN RETINA

CROSS REFERENCE TO RELATED APPLICATION

This application claims priority to U.S. Provisional Application Ser. No. 60/108,722, filed Nov. 17, 1988.

FIELD OF THE INVENTION

This invention relates generally to systems which optically scan the human eye and, more particularly, to systems that image, or project an image to the eye.

BACKGROUND OF THE INVENTION

There is considerable interest in entertainment and/or educational systems that provide a more realistic experience to a user and that do not require the substantial hardware and software typically employed by a full-field video projection system. For example, modern "virtual reality" apparatus typically include video and audio signal generators that provide signals to a headset in accordance with instructions received from a controller. The headset projects a near field image inches away from the viewer, typically completely occupying the field of the vision of the viewer's eyes. Most such virtual reality systems alter the view presented to the viewer in response to the position of the viewer's head, as sensed by the headset, such that the view changes in much the same manner that a far field image received by the human eye would vary.

While these virtual reality systems overcome the disadvantages of large projection and reflective screens found in conventional projection systems, the cumbersome headset is still a limitation. Moreover, the optical systems of the virtual reality apparatus typically still form an image on a screen, albeit a smaller screen, so as to provide the image to viewer's eyes.

It is possible present an image to a viewer by scanning the viewer's eye or eyes with a modulated beam of light. Such systems directly present the image to the viewer's retinas, thereby advantageously obviating the need for either far field or near field projection screens. Apparatus and methods for scanning the eye are known and used in systems for examining particular attributes of both the interior and exterior of the human eye.

For example, systems are known for scanning the iris of the eye and typically, include an imager which obtains a video image of the iris of each person and compares the image with known patterns stored in the system memory. The human iris is essentially unique for each individual and, unlike other forms of direct personal identification such as fingerprints, does not lend itself to alteration or misinterpretation. Iris patterns can thus be used as a basis for identification aid in controlling, for example, access to secured facilities or to an automated transaction machine (ATM). Examples of these systems are found in U.S. Pat. Nos. 5,572,596 and 5,291,560, both of which are herein incorporated by reference.

Other known systems examine retinal vasculature patterns by scanning a fixated eye with a light source arranged in a selected pattern and detecting that portion of the pattern which is reflected off of the retina. The reflected light source pattern is analyzed for each intercept of the light with a blood vessel. The intercept pattern is stored for future recall and comparison with subsequently obtained pattern(s). Identification systems can use such comparisons since, like the iris, a retinal vasculature pattern is unique and constant. The analysis is performed by one of a number of algorithms which identifies a match between the scanned and stored retinal vasculature pattern. An example of this type of device is shown in U.S. Pat. No. 4,109,237, herein incorporated by reference.

With the foregoing systems, the eye is carefully illuminated and either the retina of iris is scanned to record a detailed image. The scanning apparatus is quite precise, but is nevertheless not free of large bulky equipment and lossy optical components.

Regarding scanning to produce an image, techniques for creating virtual displays via retinal scanning of laser beams have been developed by, inter alia, the Human Interface Laboratory at the University of Washington, and commercialized via Microvision. The technology of these systems involves the modulation of laser beams directed onto the retina of the eye. By modulating the intensity as well as the vertical and horizontal sweep of a laser beam at high speed, a video-like image can be formed onto the retina. A tiny "micro machine" mirror deflects the laser beam in the horizontal and vertical axes simultaneously. As this technology develops, ever greater resolution and bandwidth will be required to deliver images which are similar to VGA, SVGA, XVGA, NTSC, HDTV etc., thus requiring the micro mirror device to be successfully modulated at extremely high frequencies.

Scanning systems such as those described above typically involve modulating a physically moving mirror in the horizontal axis at one frequency while modulating it at the same time in the vertical axis, often so as to replicate the conventional raster sweep of an electron beam of a cathode ray tube, and thus requiring the mirror or mirrors to oscillate in an unnatural way. This can require exercising considerable dynamic control and overcoming significant magnetic energy. At the same time, use of the raster scan to produce high resolution imagery over the entire field of view can require a large bandwidth.

Thus, although existing systems for scanning the eye, such as the examination and presentation systems described above, are impressive, improvements can be made. Accordingly, it an object of the present invention to overcome one or more of the aforementioned disadvantages of the prior art, such by providing methods and apparatus for the improved scanning of the eye, such as for the presentation of images to, and/or the examination of, the eye

SUMMARY OF THE INVENTION

In one aspect of the present invention, an apparatus directly projects an image onto a retina. The apparatus includes an optical source for generating a light beam to be focused on a retina. A projection device sweeps the light beam along the retina in an ellipsoidal pattern such that a higher spatial concentration of light pixels impinge a selected portion of the retina than a peripheral portion thereof. A controller is coupled to the optical source and the projection device for modulating the light beam such that a higher temporal concentration of light pixels impinge a central portion of the retina than a peripheral portion thereof.

In another aspect of the present invention, a method is provided for directly projecting an image onto a retina. A light beam is generated and swept along a retina in an ellipsoidal pattern such that a higher concentration of light pixels impinge a central portion of the retina than a peripheral portion thereof. The light beam is modulated such that a higher temporal concentration of light pixels impinge a central portion of the retina than a peripheral portion thereof.

In one aspect, the invention a system of the foregoing type which is characterized by a weighted projection function such that the more sensitive areas of the human retina selectively receive the projected image.

In another aspect, the present invention can provide a system of the foregoing type in which the image is projected into a selected zone of the human retina, reducing overall system bandwidth requirements.

In yet another aspect, the present invention includes an image projection apparatus of the foregoing type which generates pixels in an ellipsoidal sweeps that rotate around a central axis.

DETAILED DESCRIPTION OF THE PREFERRED EMBODIMENTS

Figure 1:
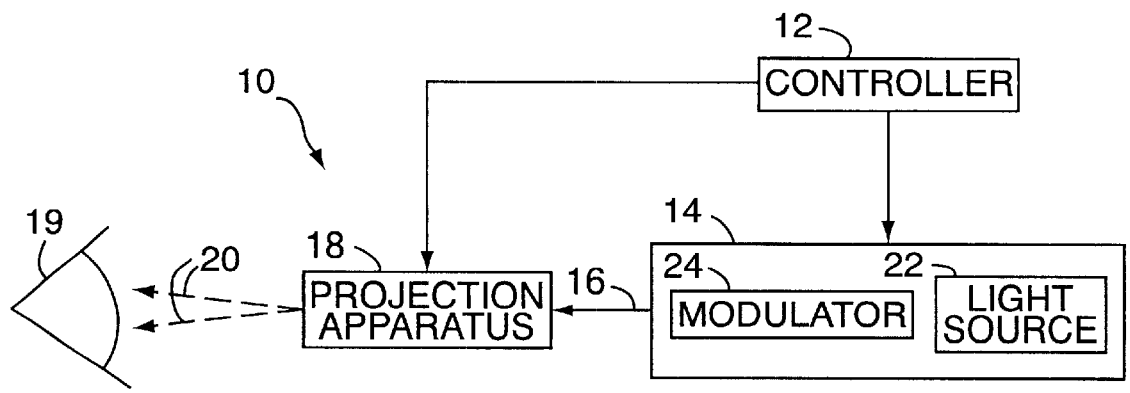
FIG. 1 is a simplified schematic illustration of a system provided by the present invention for directly projecting an optical image onto a human retina.

FIG. 1 illustrates a system 10 for projecting an image onto a human retina in accordance with the present invention. The system 10 includes a controller 12 which generates signals in accordance with an algorithm detailed hereinafter for presentation to a modulated optical source 14, which provides a modulated optical beam 16 to a projection apparatus 18. The projection apparatus scans an image onto the retina of the eye 19 of a viewer, as indicated by reference numeral 20.

The modulated light source 14 includes a laser or other light source 22, which can be used for generation of an optical image. Preferably, the light source 22 is a laser. The modulated light source 14 can also include a discrete optical modulator 24, which is addressable and receives control signals from the controller 12. The optical modulator 24 can be of a known type, and is capable of modulating an optical beam with sufficient bandwidth to allow for presentation of the image to the viewer. Those skilled in the art will note that in certain embodiments, the light source 22 may be modulated directly, without the inclusion of the discrete optical modulator 24.

Figure 2:
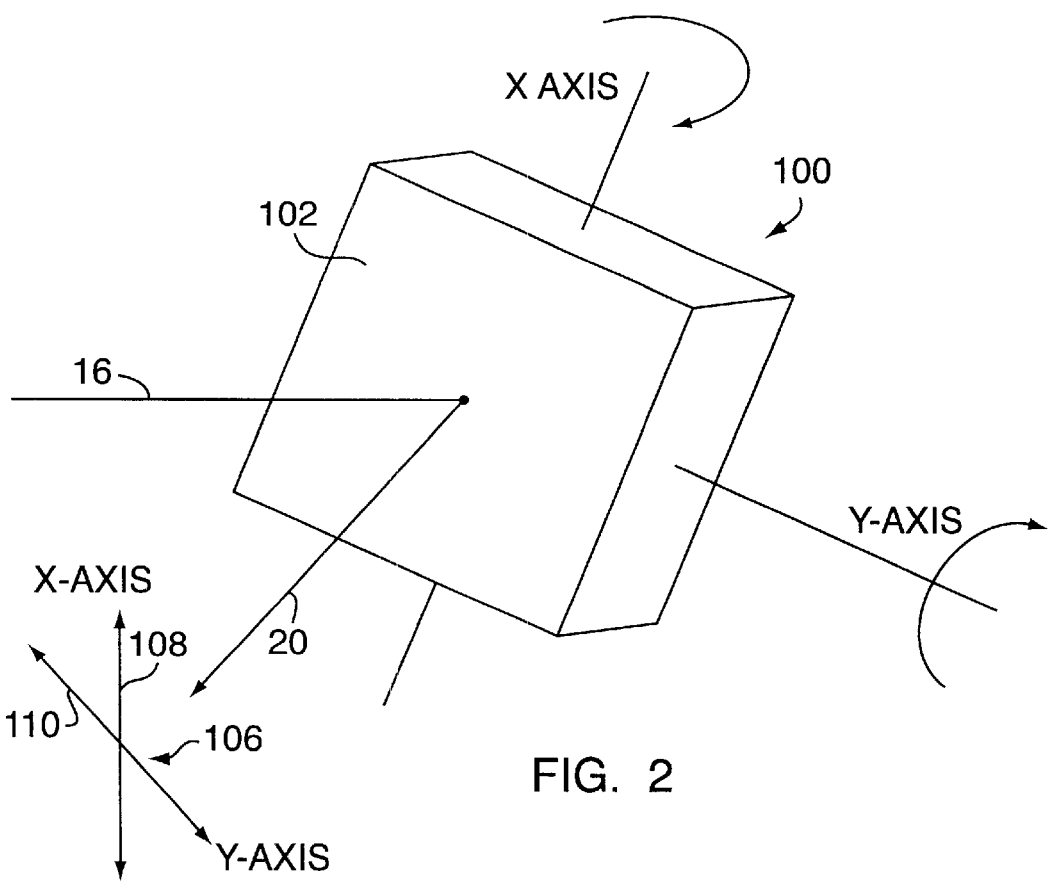
FIG. 2 is a simplified schematic illustration of a mirror used to present an image pixel to the viewer.

The projection apparatus 18 can include, in the preferred embodiment, two moveable optical mirrors, one for each eye. FIG. 2 illustrates one such mirror 100. Preferably, each mirror executes substantially the same movement in a repetitive manner, which movement, as detailed hereinafter, is a departure from the standard X-Y orthogonal raster scan. The mirror 100 has a reflective surface 102 which receives the modulated optical beam 16 and directs the beam toward the eye 19 in accordance with mirror control signals generated by the controller 12. The beam is projected into a three-dimensional retinal surface 106, having X and Y axes 108 and 110 respectively. Each mirror 100 has one or more miniature motors (not shown) for scanning along X and Y orthogonal axes or, as in the preferred embodiment, along polar coordinates.

Figure 3:
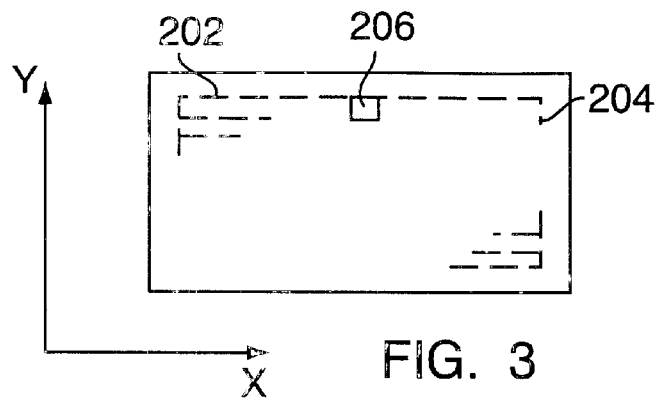
FIG. 3 is a simplified schematic illustration of a raster pattern created by a prior art imaging system.

In the prior art, the mirror 100 is typically manipulated by the motors to execute a conventional raster scan movement such that each discrete light receiving element of the eye (rod or cone) i.e., "pixel" was swept evenly in duration. The pattern is similar to that which is presented in a conventional CRT or television screen. That is, as shown in FIG. 3, a row of pixels, such as the first row including pixels 202, 204 and 206, is first fully illuminated in a fast scan (X) direction, with a indexing taking place in a columnar fashion in a slow scan (Y) direction.

Figure 4:
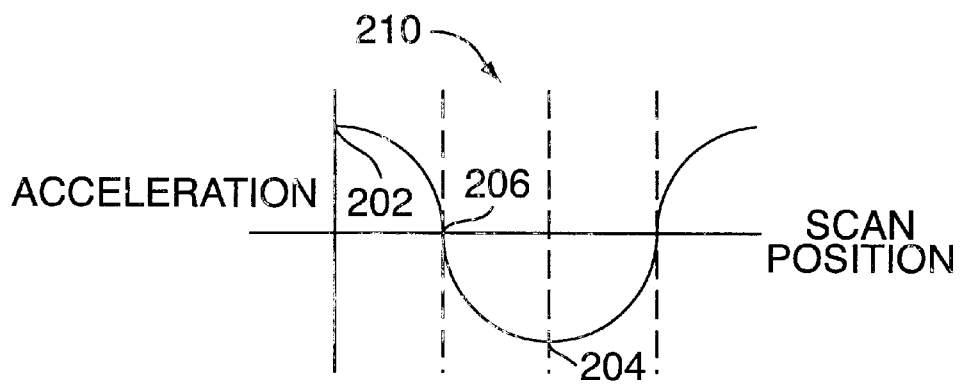
FIG. 4 is a diagrammatic illustration of the computed acceleration of the mirror of FIG. 2 according to a prior art control system.

Unfortunately, the required movement of the mirrors places tremendous strain on both the control algorithm as well as the equipment needed to accurately and repeatedly complete the raster movement. Shown diagrammatically in FIG. 4 is a simplified curve 210 of the theoretical acceleration, as a function of scan position, borne by a mirror using a prior art system. A conventional raster scanned pattern requires that the mirror undergo severe acceleration at the initial and final positions of the "pixel" row as illustrated by pixels 202 and 204 respectively, with the minimum acceleration occurring at the mid-point of the scan, illustrated by pixel 206.

FIG. 4 shows is a simplified curve 300 showing the relative velocity magnitudes as a function of scan position of the mirror as manipulated by prior art controllers. Maximum velocity occurs in the middle of the scan, as illustrated by pixels 206, with minimum velocity occurring at the extreme ends of the pixel row as illustrated by pixels 202.

In general, the projection apparatus of the prior art is sufficiently robust to undergo the rather extreme motion outlined above. Although the size and mass of the micromechanical scanner, e.g., the mirror 100, is typically small, the scanning speed is still limited by dynamic forces which do not hinder the performance of an electron beam, for example, which has no mass, and for which the raster scan technique was first developed. The mirror 100 of FIG. 2 does have a finite mass, and is typically actuated by high frequency modulated magnetic fields. Forcing the mirror 100 into a raster-scanning mode that is similar to an electron beam for a cathode ray tube demands an unnatural oscillation for such a mechanical device. Control of the modulation of the mirror at high frequencies is likely be difficult and, as noted above, the scanning speed of the laser beam limited. In addition, the effects of inertia, component tolerances and element wear can conspire seriously degrade the system performance from the optimum. Consequently, the control algorithm for the scanning often must be developed so as to compensate for these shortcomings of the raster scan technique.

According to the invention it is realized that a much more natural motion for the mirror is a simultaneous sinusoidal motion in both the x and y axes. Accordingly, in one aspect of the invention, modulated magnetic fields actuate the mirror 100 in x and y sinusoidal patterns, similar to a pendulum or Spirograph toy. This is a radical departure from raster-based image generation, and, according to the invention, a computer database of graphical imagery is addressed by the high speed graphics computer, such as can be included in the controller, such that each point (or pixel) along a sinusoidal path laser light represents an x-y pixel coordinate in the database so as to reconstruct a coherent image to a viewer.

The raster pixel control algorithm of the prior art is understood to have other disadvantages as well. The middle of the retina, where the minimum photon flux is presented due to the maximum velocity of the raster scan, is dimmer that the ends of the retina, which receive a maximum flux of photons. The prior art systems consequently must, at a minimum, compensate for the foregoing natural occurring phenomena to even the brightness of each of the pixels.

Figure 6A:
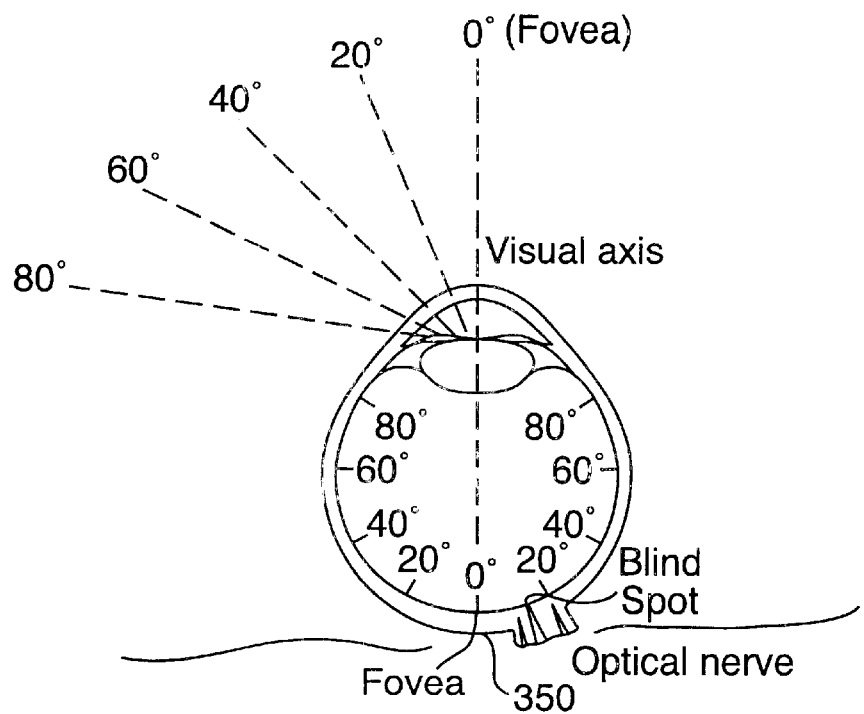
FIGS. 6A and 6B schematically illustrate a typical eye, with FIG. 12B being a view of the eye of FIG. 6A taken along section line 6B—6B of FIG. 6A.
Figure 6B:
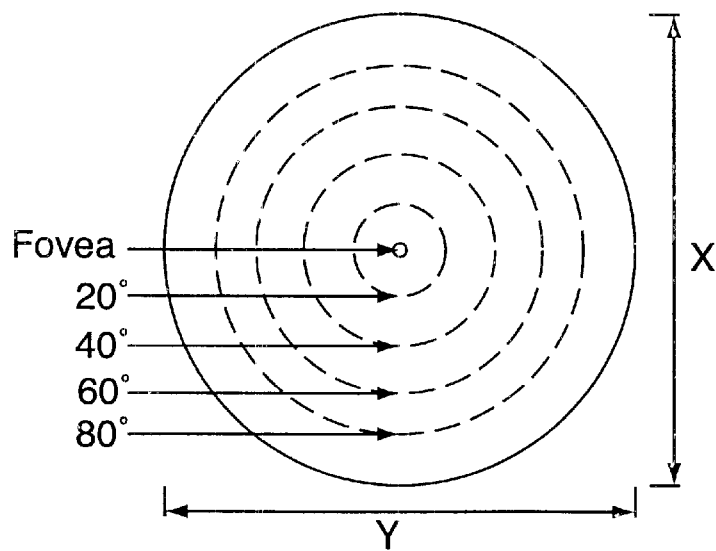

However, a more fundamental problem arises from the underlying human physiology. The retina is more sensitive to light in certain areas. As is known, the central region of the human retina is primarily responsible for the majority portion of the image that is generated by the brain. It is well known that the human eye has a foveal area where high-resolution imagery is gathered. Outside the foveal area, the human eye's acuity rapidly falls off. See FIGS. 6A, 6B and 13, where FIGS. 6A and 6B schematically illustrate the retina, and FIG. 7 illustrates the concentration of rods and cones as a function of the angles shown in FIGS. 6A and 6B.

Figure 7:
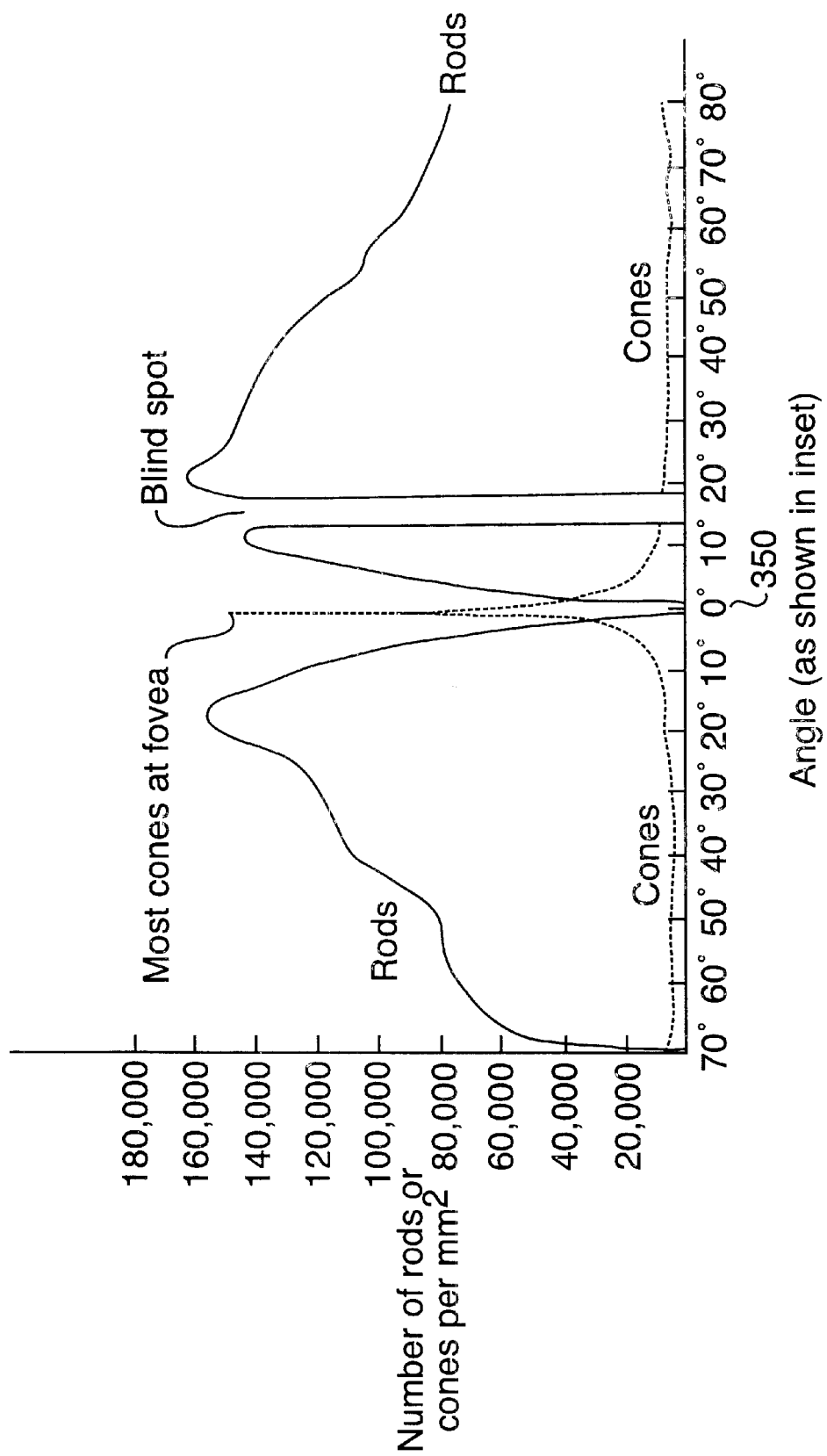
FIG. 7 illustrates the concentration of rods and cones as a function of the angles shown in FIGS. 6A and 6B.

As shown in FIG. 7, there is an extremely high concentration of image-sensing cones at the eye's fovea 350, with rapidly declining cone concentration as a function of distance from the fovea to the periphery of the retina. At a small distance from the fovea 350 the human eye has very poor ability to resolve sharpness or color. The human visual cortex and brain does enormous processing to integrate the entire visual field into a cohesive image.

Figure 5:
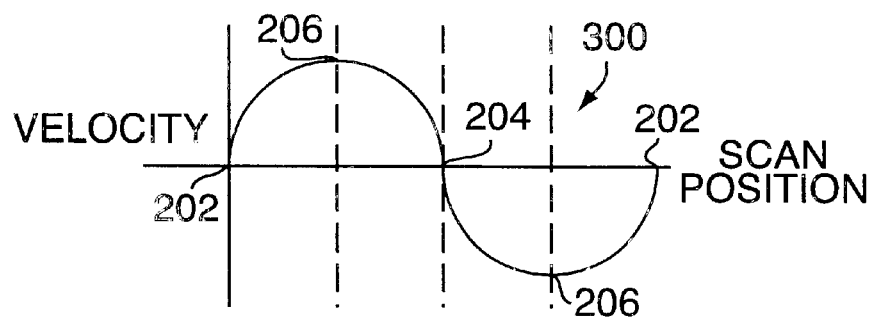
FIG. 5 is a diagrammatic illustration of the velocity profile of the mirror surface as generated by a prior art control system.

Consequently, according to another aspect of the invention, the retinal illumination is center-weighted, which can be the inverse of the illumination generated by some prior art control algorithms. An uncompensated illumination algorithm having the characteristics shown with respect to FIGS. 3–5 typically results in maximum brightness occurring in regions which are not primary contributors to the image in the brain.

Moreover, since the central portion of the retina provides the vast majority of signals that form the image in the brain, evenly illuminating the entire retina consumes excessive system bandwidth and control requirements. In certain practices of the invention, illumination of just the central portion can be sufficient to create the desired image.

Figure 8:
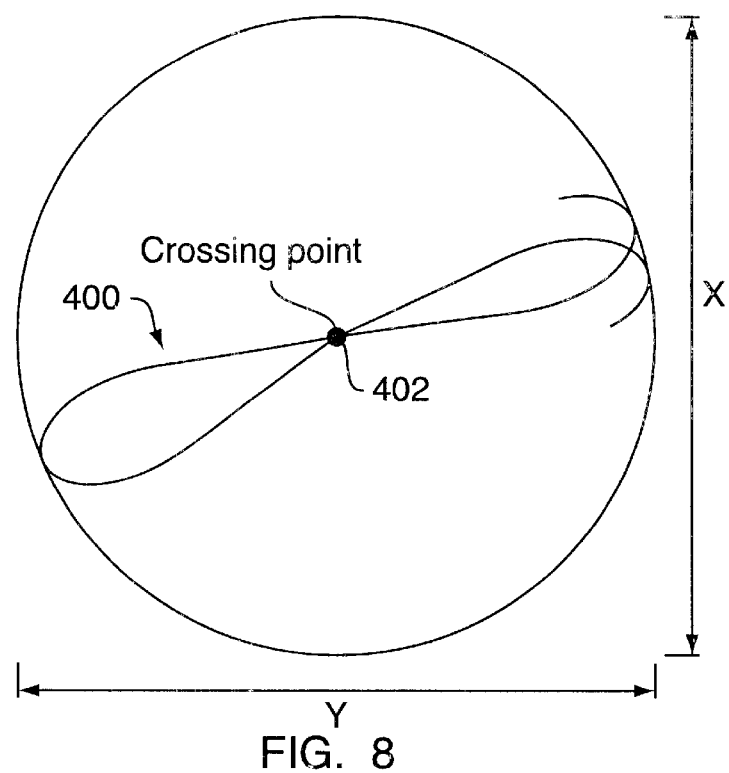
FIG. 8 illustrates a laser beam swept in a sinusoidal pattern on the x-y field such that the sweep crosses at a crossing point.
Figure 9:
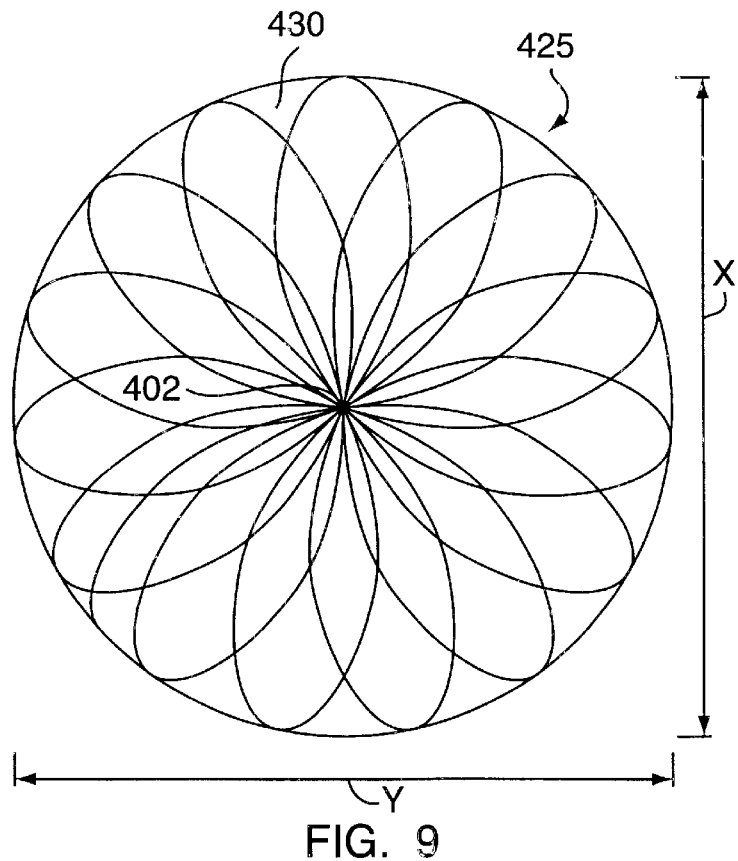
FIG. 9 illustrates a "frame" of an image as represented by a circular field of sinusoidal sweeps of FIG. 8.

According to the invention, the laser beam can be swept in sinusoidal patterns in such a manner that each sweep, such as the sweep 400 shown in FIG. 8 of the sinusoidally modulated laser beam crosses at a single point 402 in the x-y field, while the sweep precesses, so that a "frame" of image is represented by a circular field such as that indicated by the reference numeral 425 in FIGURE. The crossing point 402 can be moved to any position within the field, via proper modulation of the mirror 100. As the laser beam is swept through a spiral pattern, it can be modulated in brightness and focus so that as the beam sweeps through the single point 802 it is highly focused, yet much less bright. As the beam sweeps away from the point, it can grow grows brighter and less focused, so that the resultant circular field 425 is of even apparent brightness. In this manner the beam crossing point 802 can be of extremely high resolution (since virtually every sweep passes through it) and of extremely high temporal information (since each sweep represents a small fraction of a "frame" representing one complete spiral sweep filling the entire circular field such as illustrated in FIG. 9. For example, one complete spiral sweep of the circular field could occur in one-sixtieth (1/60th) of a second, and consist of 525 precessing sinusoidal sweeps; thus, the field could contain the same information as a field of NTSC video. In contrast to this focus point of all sweeps, the periphery 430 of the field drops off in clarity and information responsive, such as in direct proportion, to the distance from the focus point. At the periphery 430 of the field, resolution is low. Thus, the visual information of a frame (or field) of an image is more concentrated at the crossing point 802, and more diffuse at the periphery 430.

Preferably, according to the present invention, the mirror 100 oscillates sinusoidally, such as in an ellipsoidal pattern, which causes the formation of high-resolution imagery in a concentrated zone, while substantially lowering resolution in a circular field around that zone. By coupling the location of this zone of high resolution to the eye's foveal area via an eye tracking mechanism, as discussed below, a very high apparent resolution image is provided. System bandwidth requirements are reduced.

Accordingly, one aspect of the present invention is a method for electing a variable resolution image from a high-speed graphics computer. Rather than a standard pixel grid in the horizontal and vertical axes, the computer can be tasked to generate pixels in an ellipsoidal sweep with a rotating central axis. This concentrates a large number of pixels into a central zone.

Another aspect of the present invention provides for modulating and focusing the laser beam in such a manner that an even field of apparent brightness is achieved. As noted above, one of the disadvantages of the known raster scan systems is uneven brightness caused by the excessive beam dwell at the extremes of each scan line. Similarly, the preferred polar scan concentrates light in the central foveal area. An adjustment to the beam intensity evens the illumination between regions.

In the preferred embodiment, the concentration of illumination (pixels) in the central zone caused ellipsoidal scan is compensated for by reducing the brightness in the center of the field, and increasing the brightness at the edge of the field, thereby producing an apparently evenly illuminated field. As the laser beam scans away from the central zone, it is also defocused in some embodiments, so that rather than sharp pixels, the pixels are graduated in focus so that they are least focused at the field edge, thus merge together to form a low resolution, yet evenly illuminated field at the edge.

Figure 10A:
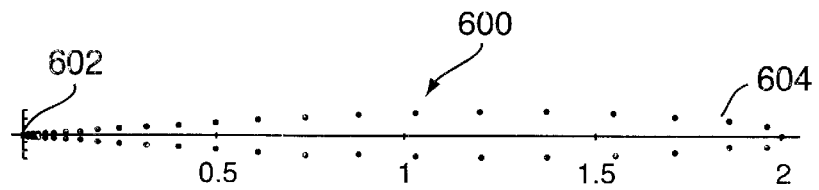
FIG. 10A is a simplified diagrammatic illustration of a portion of an elliptical trace 600 generated by a controller and projection apparatus used by the present invention.

FIG. 10A is a simplified diagrammatic illustration of a portion of an elliptical trace 600 generated by a controller and projection apparatus used by the present invention. The pixel presentation is weighted more towards the center of the eye at 602, both in a temporal and a spatial manner. That is, the illumination of the outer portions of the retina at 604 is done with a fewer number of pixels and for less time than occurs in prior art raster scan systems. The pixels are more closely spaced and, hence, more information is transmitted to the eye with less bandwidth than would be required in a rectangular raster scan presentation of image pixels by prior art systems.

Figure 10B:
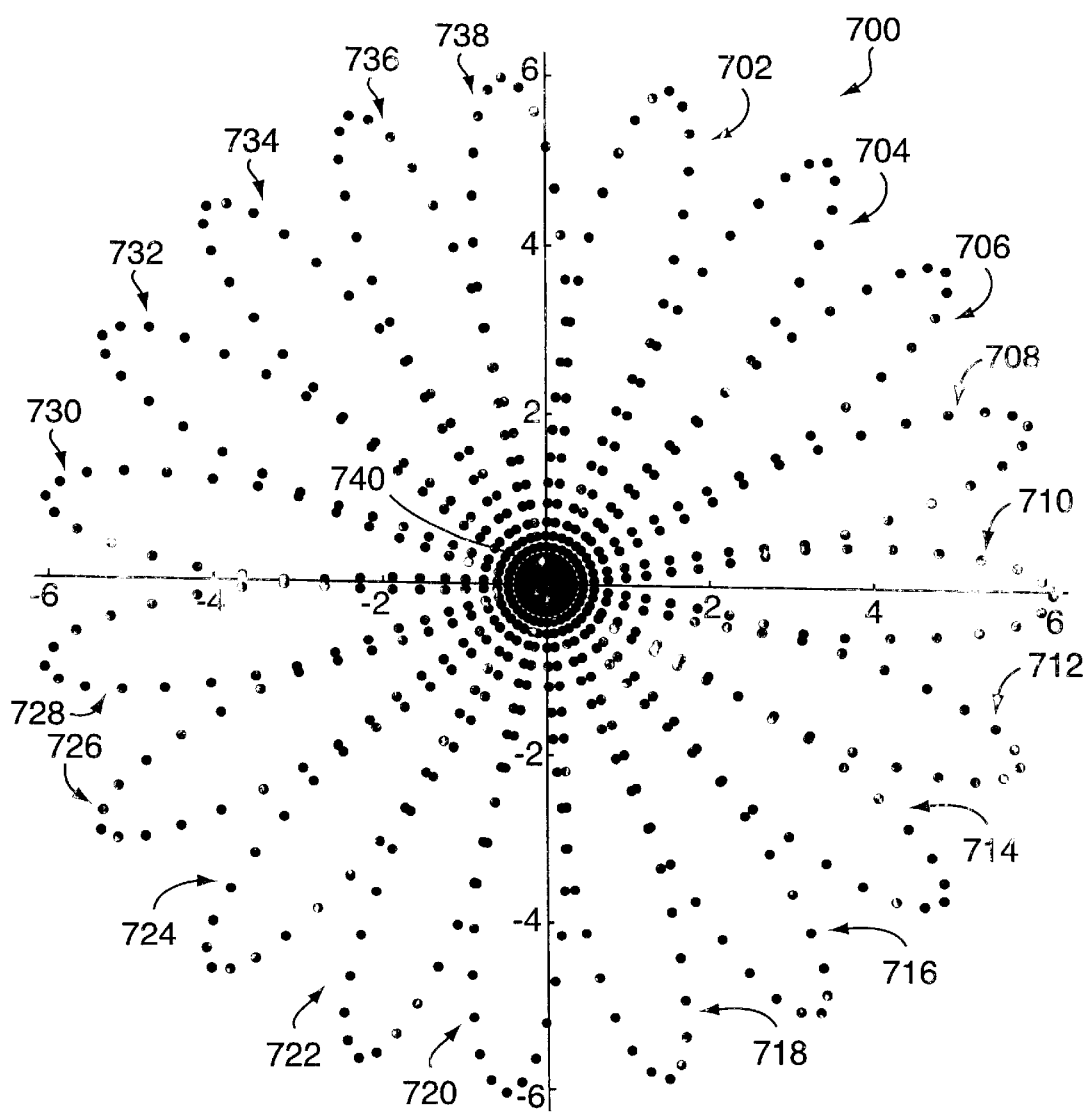
FIG. 10B is a simplified schematic illustration of a portion of a scan 700 provided by the controller of the present invention FIG. 11, where sweeps 400 are shown superimposed on the retina 375, so as to achieve true "virtual reality" which replicates the human eye's almost 180-degree field of view

FIG. 10B is a simplified schematic illustration of a portion of a scan 700 provided by the controller of the present invention. The scan corresponds to a plurality of individual elliptical scans 702–703 which are, in essence, rotated in polar fashion about the central axis of the eye at 740 providing for substantial illumination of the central region of the eye as opposed to the periphery. Moreover, the control algorithm required for elliptical motion of the mirror and hence, the pixel undergoes far less severe acceleration and deceleration as compared to that required of the conventional X and Y orthogonal raster scans. Thus, according to the invention, methods and apparatus are provided for trading off visual information between the fovea and retinal periphery so that the resulting image presented to a viewer more accurately resembles natural human vision clarity, without resultant increase in image density or bandwidth which would be required to fill the entire field with equally sharp detail.

Figure 11:
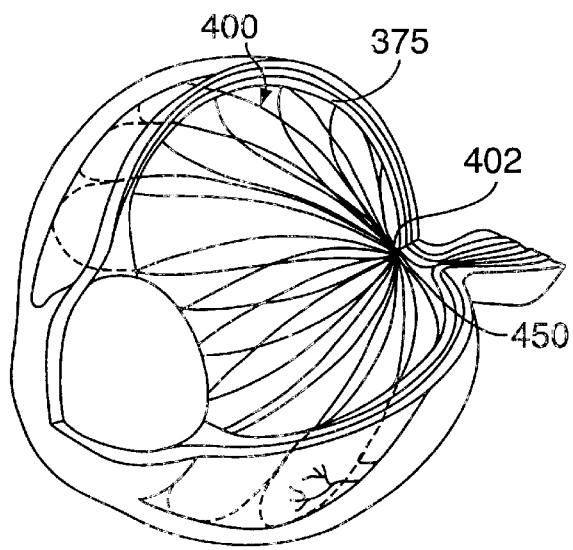

Preferably, the sweeping occurs in such a manner as to fill virtually the entire human retina 375 with image, as illustrated in FIG. 11, where sweeps 400 are shown superimposed on the retina 375, so as to achieve true "virtual reality" which replicates the human eye's almost 180-degree field of view. According to the invention, optics are provided that take advantage of the unique attributes of laser beams to enter the human eye, pass through the cornea and lens, and arrive on the retina, typically without the conventional huge and heavy optical apparatus to create a large entrance pupil for the eye.

Figure 12A:
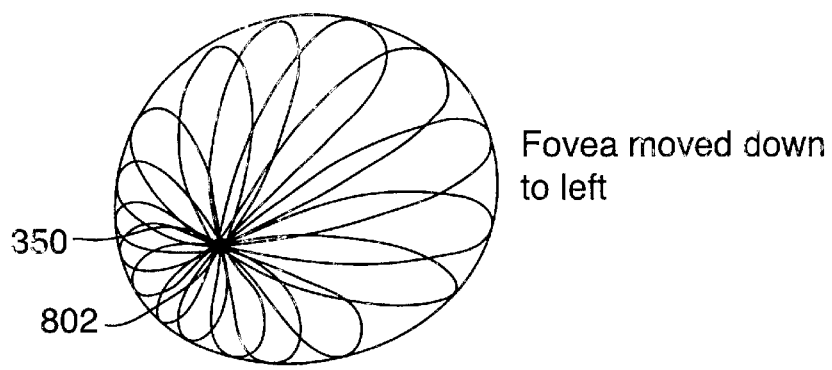
FIGS. 12A and 12B illustrate modulating the crossing point of all sweeps to correspond to the instantaneous location of the fovea.
Figure 12B:
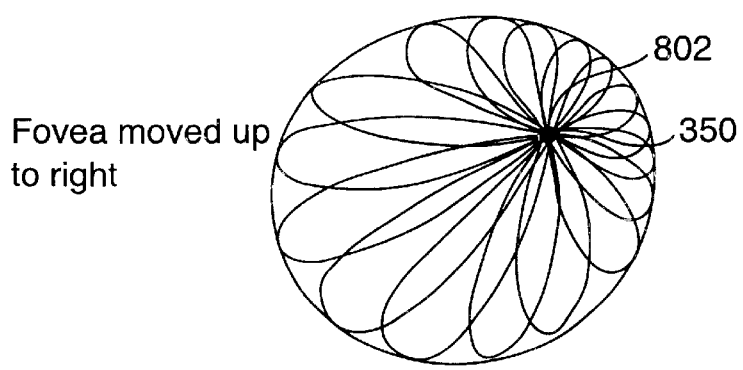

Known in the art are methods and apparatus for tracking the eye. According to the invention the eye can be tracked and the "crossing point" ( e.g., point 402 of FIG. 8) of all sweeps is modulated to correspond to the location of the fovea 350 at that instant, as illustrated in FIGS. 12A and 12B. The overall sweep area can remain constant. In this way, the eye tracking apparatus can provide "real-time" foveal location data for virtually every sweep of the beam in the overall field. Preferably there is little or no latency in the provision of accurate foveal information from the eye tracking sensor(s), using a look-up table or other such aligning algorithm. Rather than waiting for the next whole frame of data, such as in standard practice, which could cause objectionable latency, each sweep of the beam should be controlled according to the latest data regarding the location of the fovea. Thus, another aspect of the includes the method and apparatus for tracking the eye and linking with the display apparatus so that the zone of high-resolution remains aligned with the fovea. This process is performed for both eyes, so that a stereoscopic image is presented.

Furthermore, according to the invention the brightness, color saturation, focus of the foveal area, as well as the entire field of the image are modulated in such a manner as to exactly track the functioning of the human eye's movement. Some of this function can be controlled by modulating the laser beam itself, via known methods and apparatus, such as those developed by Microvision, while additional modulation the brightness, color saturation, and focus of the image (or parts of it) can be controlled by graphic image processing.

It is also well known that the focus and convergence of the two human eyes are closely linked. Another aspect of this invention is the methodology for linking the eye tracking of each eye to a convergence detection method so that as the eyes naturally converge to imagery at a certain distance (as a result of the displayed convergence of two computer graphics images left eye, right eye) the laser beam(s) can be modulated in focus as well, so that imagery outside the area of convergence (and interest) is appropriately defocused in a natural way.

Figure 13A:
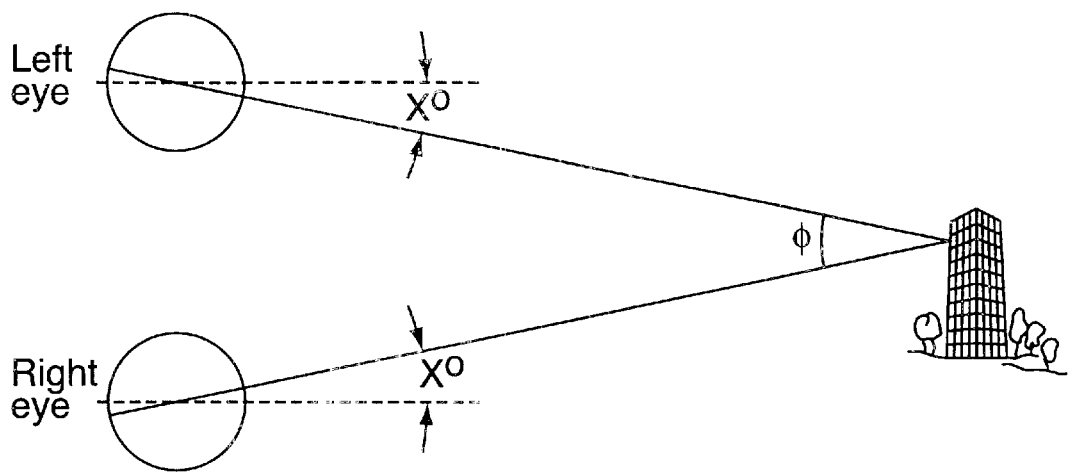
FIGS. 13A and 13B illustrate the variation of the angle of convergence of the eyes with the distance from the eye to the object being viewed.
Figure 13B:
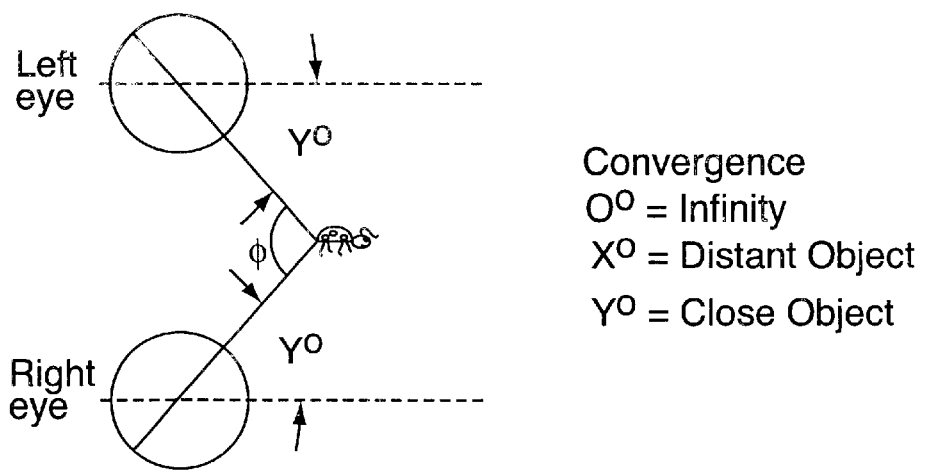

For example, as eye tracking systems can determine the exact direction in which the eye is looking, eye tracking data from both eyes can provide differential data relating to convergence of the eyes upon subject matter at various distances, such as illustrated in FIGS. 13A and 13B. The convergence angle, $\phi$, is smaller for objects that are far away, as in FIG. 13A, and larger for near objects, as in FIG. 13B. A full virtual retinal display can be provided with full stereoscopic function such that selective data is displayed as a function of distance. For example, in an aircraft cockpit, a pilot wearing a virtual retinal display system, as described above, could converge his or her eyes to the natural distance of flight deck displays and controls. Using a servo loop algorithm, computerized data related to such displays could be brought into focus, increased in brightness and color saturation, etc., while simultaneously defocusing and dimming other computerized data, such as a virtual certain display which would otherwise only be emphasized when the pilot converges his/her eyes near infinity. In this way, the eye convergence sensing system can be connected directly to the database of all possible imagery available, such as near focus instruments, further away controls, further distance flight deck components, such as breakers and navigation aids, then out-of-cockpit imagery, such as horizon indicators, "highway-in-the-sky" flight paths, other aircraft and terrain. At each convergence distance that particular data is highlighted by focusing, brightening, and color enhancing, while other data which is either nearer or farther from the convergence distance, is defocused, dimmed and color desaturated. The viewer (a pilot, for example) can be provided with switchable controls to consciously select or deselect desired information for display.

In another embodiment, a convergence sensing algorithm can offer the ability to display with full fidelity only that data which is converged upon at any one time, such that the graphic engine of the computer can concentrate its energies only on specific convergence selected imagery in the foveal areas of the eyes. In this way, the human visual cortex and brain senses the world in the most natural possible fashion, potentially with full human visual fidelity, at a fraction of the bandwidth and computing power which would be required to fill the entire human visual field and all distances with fully rendered imagery.

U.S. Pat. Nos. 5,467,104 and 5,659,327, issued on Nov. 14, 1995 and Aug. 19, 1997, respectively, and entitled "Virtual Retinal Display," disclose methods and apparatus for manipulating laser beams on the retina. Both are herein incorporated by reference.

Another aspect of this invention is the utilization of other manotechnology mirror devices which both rotate and process in a manner as described in the accompanying formulas and illustrations. This would greatly simplify the need for complex mirror management electronic processes to overcome the natural inertia and harmonics of the mirror device itself.

Although the invention has been shown and described with respect to a preferred embodiment thereof, it would be understood by those skilled in the art that other various changes, omissions and additions thereto may be made without department from the spirit and scope of the present invention. For example, as understood by one of ordinary skill in the art, the techniques and apparatus described above can be applied to scanning so as to examine the eye, as well as for projecting an image for viewing by the eye.

What is claimed is:

1. An apparatus for direct projection of an image onto a retina, the apparatus comprising:

an optical source for generating a light beam to be focused on a retina;

a projection device for sweeping the light beam along the retina in an elliptical pattern such that a higher spatial concentration of light pixels impinge a central portion of the retina than a peripheral portion thereof; and a controller coupled to the optical source and the projection device for modulating the light beam such that a higher temporal concentration of light pixels impinge a central portion of the retina than a peripheral portion thereof.

2. An apparatus as defined in claim 1, wherein the optical source includes a laser.

3. An apparatus as defined in claim 1, wherein the optical source includes an optical modulator for modulating the light beam in response to the controller.

4. An apparatus as defined in claim 1, wherein the projection device includes an optical mirror and a motor coupled to the mirror for moving the mirror to sweep the light beam along the retina.

5. An apparatus as defined in claim 1, wherein the controller includes means for controlling the optical source to decrease the brightness of the light beam when sweeping the central portion of the retina and increasing the brightness of the light beam when sweeping the peripheral portion thereof to thereby compensate for an increased concentration of light pixels impinging the central portion of the retina.

6. An apparatus for projecting an image onto the retina of an eye with a light beam, the apparatus comprising:

a controller;

a projection device for sweeping a light beam across the retina;

a modulated optical source for providing the light beam to the projection device, wherein said projection device, and wherein said controller controls said projection device so as to sweep the light beam across the retina in a succession of precessing and crossing sweeps, and controls the modulated optical source to modulate the light beam so as to provide the image to the retina.

7. A method of directly projecting an image onto a retina, the method comprising the steps of:

generating a light beam; sweeping the light beam along a retina in an ellipsoidal pattern such that a higher concentration of light pixels impinge a central portion of the retina than a peripheral portion thereof; and modulating the light beam such that a higher temporal concentration of light pixels impinge a central portion of the retina than a peripheral portion thereof.

8. A method as defined in claim 7, wherein the generating step includes generating a laser beam.

9. A method as defined in claim 7, wherein the step of sweeping includes moving a mirror to deflect the light beam onto the retina.

10. A method as defined in claim 7, further including the step of decreasing the brightness of the light beam when sweeping the central portion of the retina and increasing the brightness of the light beam when sweeping the peripheral portion thereof to thereby compensate for an increased concentration of light pixels impinging the central portion of the retina.

11. A method of providing an image to a viewer, comprising:

providing a light beam;

sweeping a light beam across the retina of an eye of the viewer in a succession of crossing and precessing sweeps; and modulating the light beam so as to provide the image to the viewer.

* * * * *